United States Patent
Kudou

(10) Patent No.: US 7,953,269 B2
(45) Date of Patent: May 31, 2011

(54) METHOD FOR INSPECTING PATTERN DEFECT OCCURED ON PATTERNS FORMED ON A SUBSTRATE

(75) Inventor: Kenji Kudou, Kawasaki (JP)

(73) Assignee: Fujitsu Semiconductor Limited, Yokohama (JP)

( * ) Notice: Subject to any disclaimer, the term of this patent is extended or adjusted under 35 U.S.C. 154(b) by 990 days.

(21) Appl. No.: 11/777,630

(22) Filed: Jul. 13, 2007

(65) Prior Publication Data
US 2007/0258636 A1    Nov. 8, 2007

Related U.S. Application Data

(63) Continuation of application No. PCT/JP2006/300349, filed on Jan. 13, 2006.

(30) Foreign Application Priority Data

Jan. 14, 2005 (JP) .................................. 2005-008158

(51) Int. Cl.
*G06K 9/00* (2006.01)

(52) U.S. Cl. ................ 382/141; 250/206.1; 250/559.45; 356/237.2; 382/144

(58) Field of Classification Search ............... 356/237.4, 356/239.8, 243.1; 382/141, 144, 145, 147, 382/149, 199, 266
See application file for complete search history.

(56) References Cited

U.S. PATENT DOCUMENTS

| | | | |
|---|---|---|---|
| 4,532,650 A * | 7/1985 | Wihl et al. ..................... | 382/144 |
| 5,046,109 A * | 9/1991 | Fujimori et al. ............... | 382/144 |
| 5,475,766 A * | 12/1995 | Tsuchiya et al. .............. | 382/144 |
| 5,539,514 A * | 7/1996 | Shishido et al. ........... | 356/237.4 |
| 5,574,800 A * | 11/1996 | Inoue et al. ................... | 382/149 |
| 5,978,503 A * | 11/1999 | Jin ................................ | 382/147 |
| 6,529,621 B1 | 3/2003 | Glasser et al. | |
| 7,269,280 B2 * | 9/2007 | Hiroi et al. .................... | 382/149 |
| 7,352,901 B2 * | 4/2008 | Fujieda ......................... | 382/199 |
| 2001/0012390 A1 * | 8/2001 | Watanabe ..................... | 382/144 |
| 2001/0055415 A1 * | 12/2001 | Nozaki ......................... | 382/141 |
| 2003/0031356 A1 * | 2/2003 | Sasa ............................. | 382/145 |
| 2003/0142860 A1 | 7/2003 | Glasser et al. | |
| 2003/0174877 A1 * | 9/2003 | Aiger ............................ | 382/145 |
| 2003/0197857 A1 * | 10/2003 | Yamashita ................. | 356/237.2 |
| 2003/0201410 A1 * | 10/2003 | Nagamura ............... | 250/559.45 |
| 2003/0206027 A1 * | 11/2003 | Nozoe et al. .................. | 324/751 |
| 2004/0008880 A1 * | 1/2004 | Horie et al. ................... | 382/144 |
| 2005/0002554 A1 * | 1/2005 | Schulze et al. ................ | 382/144 |
| 2007/0258636 A1 * | 11/2007 | Kudou .......................... | 382/149 |

FOREIGN PATENT DOCUMENTS

JP    58-147114 A    9/1983

(Continued)

OTHER PUBLICATIONS

International Search Report of PCT/JP2006/300349, date of mailing Apr. 18, 2006.

*Primary Examiner* — Gregory M Desire
(74) *Attorney, Agent, or Firm* — Westerman, Hattori, Daniels & Adrian, LLP

(57) ABSTRACT

In a pattern-defect inspection method for inspecting a defect in an inspection pattern by comparing an image of the inspection pattern with an image of a reference pattern, inspection sensitivity is adjusted in accordance with the number of corner portion and so on of the reference pattern.

10 Claims, 17 Drawing Sheets

FOREIGN PATENT DOCUMENTS

| | | |
|---|---|---|
| JP | 61-86639 A | 5/1986 |
| JP | 2002-244275 A | 8/2002 |
| JP | 2002-532760 A | 10/2002 |
| JP | 2004-45066 A | 2/2004 |
| JP | 2004-191297 A | 7/2004 |
| JP | 2005-215400 A | 8/2005 |

* cited by examiner

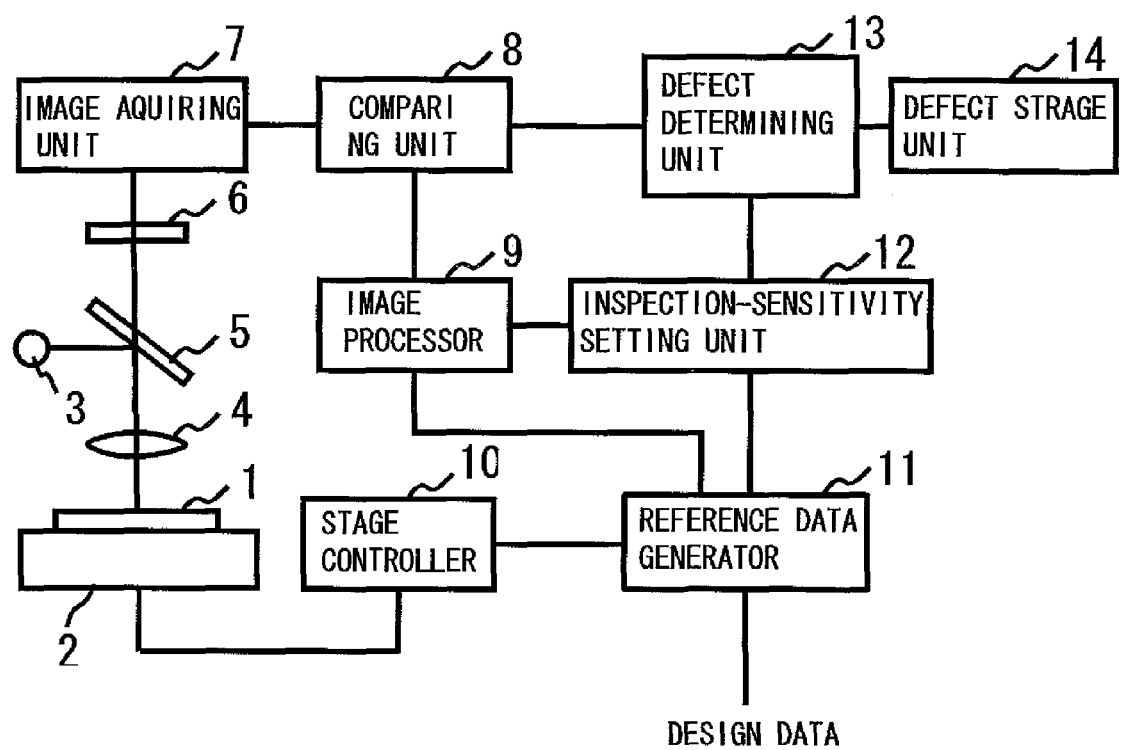

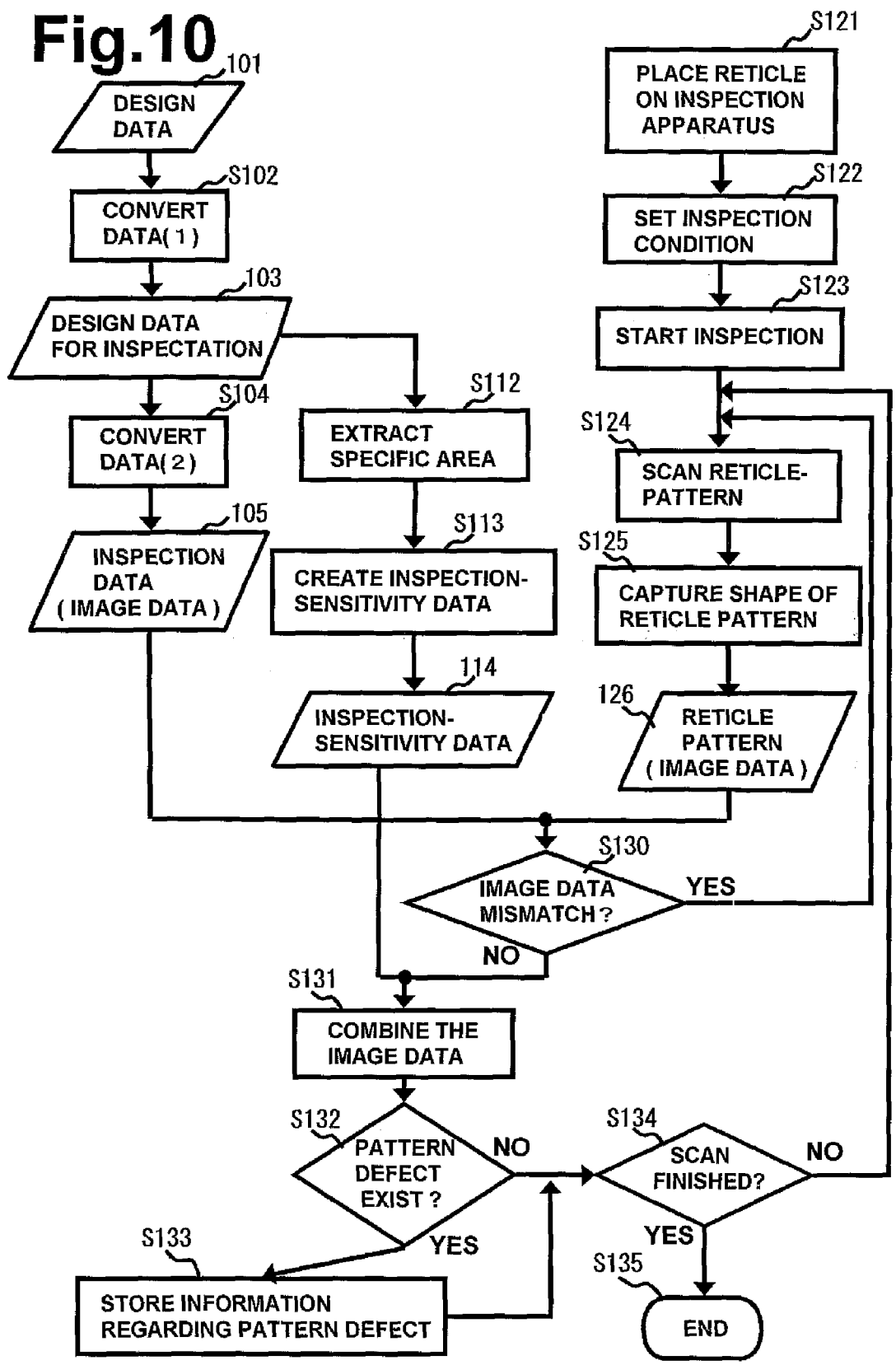

INSPECTION DATA

INSPECTION-SENSITIVITY DATA

RETICLE PATTERN

COMBINATION PATTERN

DEFFERENCE BETWEEN INSPECTION DATA AND RETICLE PATTERN (E)

INSPECTION-SENSITIVITY DATA (F)

(E) + (F)

Fig.15
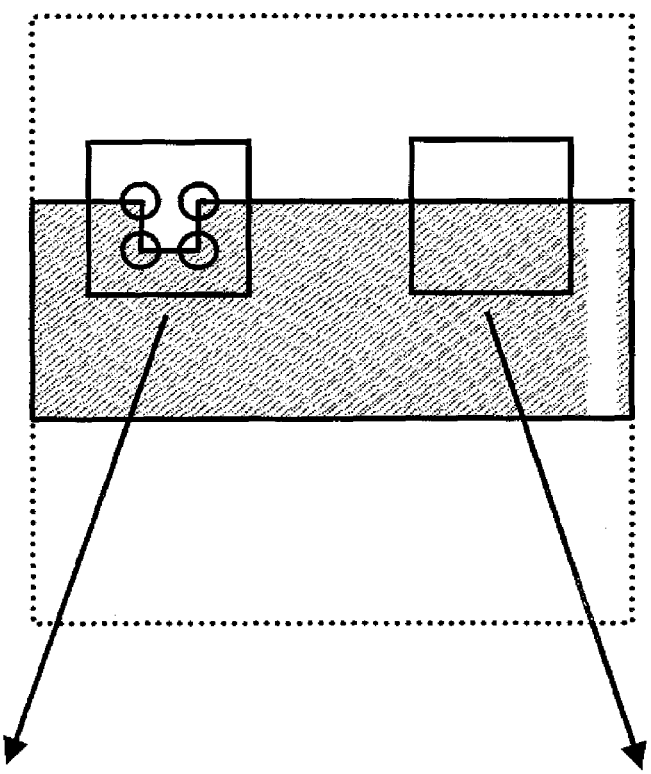
DESIGN DATA
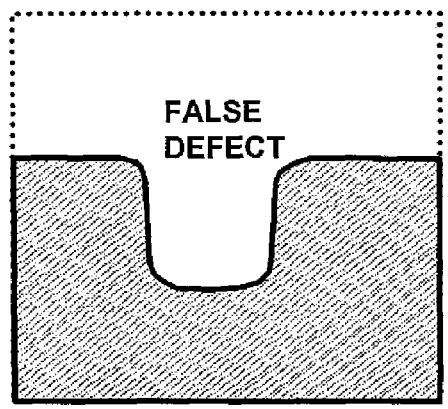
RETICLE PATTERN SHAPE A
FALSE DEFECT
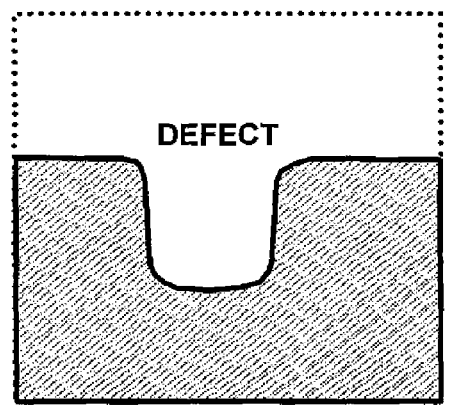
RETICLE PATTERN SHAPE B
DEFECT

METHOD FOR INSPECTING PATTERN DEFECT OCCURED ON PATTERNS FORMED ON A SUBSTRATE

BACKGROUND OF THE INVENTION

1. Field of the Invention

The present invention relates to methods for pattern defect inspection and semiconductor-device manufacturing methods involving the pattern defect inspection. In particular, the present invention relates to a method for pattern defect inspection for reticles or semiconductor wafers and a semiconductor-device manufacturing method involving the pattern defect inspection.

2. Description of the Related Art

Manufacture of semiconductor ICs (integrated circuits) requires inspection as to whether or not patterns are properly formed on reticles or semiconductor wafers as designed. Typically, such a pattern-defect inspection employs a method in which inspection patterns, such as reticle patterns or wafer patterns, are compared with a reference pattern drawn based on design data to detect differences between the inspection patterns and the reference pattern.

In the case of reticles, reticle patterns are made of chrome patterns formed on quartz substrates through photolithography and dry etching. Differences from the reference pattern are mainly due to chrome pinholes or chrome deposits produced by photolithography and dry etching.

When such a difference in pattern shape is small to an extent that does not affect the operation of a semiconductor IC, it does not substantially act as a defect. Accordingly, a permissible value for differences from the reference pattern is predetermined for the pattern-defect inspection, so that an inspection pattern is regarded as a defect when a detected pattern difference exceeds the threshold.

The term "threshold" herein refers to a value that defines inspection sensitivity for the pattern defect inspection. In order to increase the inspection sensitivity, the threshold is set to a low value, and in order to reduce the inspection sensitivity, the threshold is set to a high value.

The threshold is typically set to a value having a predetermined added margin (for increasing the inspection sensitivity) so that all of produced defects can be detected. Consequently, patterns that are supposed to be non-defective are also determined as defects and are processed, thus requiring a large amount of time to perform correction in a subsequent process. Of defects detected in this manner, defects that do not substantially act as defects are referred to as "false defects".

Conversely, setting inspection sensitivity too low results in the failure of detecting true defects, thus reducing the yield of semiconductor ICs. Therefore, it is necessary to set appropriate inspection sensitivity for the pattern defect inspection, considering the yield, inspection time, and so on.

In general, for different reticles or even for the same reticle, influences that pattern differences have on device characteristics differ from each other depending on places where the patterns are formed; therefore, an appropriate value for inspection sensitivity to be set also varies. In many cases, the inspection sensitivity is set to the same value for all reticles used in the manufacture of the same semiconductor IC. Thus, in such cases, the inspection sensitivity must be adjusted to the inspection sensitivity of a portion requiring the highest inspection sensitivity. Thus, there is a problem in that the inspection sensitivity for other portions becomes too high.

Accordingly, a method in which a reticle is divided into multiple inspection areas and inspection sensitivities that are different from each other for the inspection areas are set has been proposed. In this case, how the inspection sensitivity for each inspection area is set is determined according to the functions of wiring patterns provided in the inspection area. Specifically, for example, as disclosed in Japanese Unexamined Patent Application Publication No. 2004-45066, a wide signal line and a narrow power line are assigned inspection sensitivities that are different from each other, considering that the likelihoods of occurrence of failures, such as line breakage, in the respective lines are significantly different from each other.

As in the example described above, with respect to patterns having very simple shapes, such as a signal line and a power line, it is possible to appropriately set inspection sensitivity. However, with respect to more complicated and smaller pattern shapes, it is difficult to set appropriate inspection sensitivity, due to problems as described below.

A majority of the aforementioned chrome pinholes or chrome deposits are caused by dust attached to the reticle surface during the pattern formation process.

Differences between inspection patterns and the reference pattern are caused by not only the above-described factors but also, for example, an excess or shortage of the amount of exposure in the photolithography, an excess or shortage of dry etching, or the like. In cases in which the differences are caused by such an excess or shortage, differences from the reference pattern also occur. For example, when the chrome layer is excessively etched, the pattern width is reduced, which results in detection of a pattern difference from the reference pattern.

As the pattern shape becomes more completed and smaller, interference due to the proximity effect and so on during exposure becomes more prominent, and consequently, the pattern difference tends to become larger.

In the known pattern-defect inspection, however, when a difference from the reference pattern is defected, a determination is made as to whether or not the detected difference exceeds a pre-set threshold without considering a cause of the occurrence of the pattern difference. As a result, there is a problem in that many false defects, which should not be to be detected, are detected. In addition, there is a problem in that a large amount of time and effort is required to subsequently remove such false defects.

SUMMARY OF THE INVENTION

According to an aspect of an embodiment of the invention, a pattern-defect inspection method for a plurality of pattern on a substrate includes extracting information of an image of a pattern on the substrate to be inspected, providing a reference pattern information from design information, the reference pattern information corresponding to the pattern to be inspected, determining an inspection sensitivity in accordance with the number of corner portions of the reference pattern, comparing the information of the image of the pattern to be inspected and the reference pattern information, and detecting a defect of the pattern by the use of the inspection sensitivity.

According to another aspect of an embodiment of the invention, a pattern-defect inspection method for a plurality of pattern on a substrate includes extracting information of an image of a pattern on the substrate to be inspected, providing a reference pattern information from design information, the reference pattern information corresponding to the pattern to be inspected, determining an inspection sensitivity in accordance with an angle of a corner potion of the reference pattern, comparing the information of the image of the pattern to be inspected and the reference pattern information, and detecting a defect of the pattern by the use of the inspection sensitivity.

According to another aspect of an embodiment of the invention, a pattern-defect inspection method for a plurality of pattern on a substrate includes extracting information of an image of a pattern on the substrate to be inspected, providing a reference pattern information from design information, the reference pattern information corresponding to the pattern to be inspected, determining an inspection sensitivity in accordance with a distance between adjacent corner potions of the reference pattern, comparing the information of the image of the pattern to be inspected and the reference pattern information, and detecting a defect of the pattern by the use of the inspection sensitivity.

BRIEF DESCRIPTION OF THE DRAWINGS

FIG. 1 is a block diagram showing a pattern-defect inspection apparatus according to an embodiment of the present invention;

FIG. 10 shows an inspection flow according to a fifth embodiment of the present invention;

FIG. 15 shows an example in which a false defect and a defect are distinguished from each based on the number of corner-portion counts according to the fifth embodiment of the present invention;

DESCRIPTION OF THE PREFERRED EMBODIMENTS

Figure 2A:
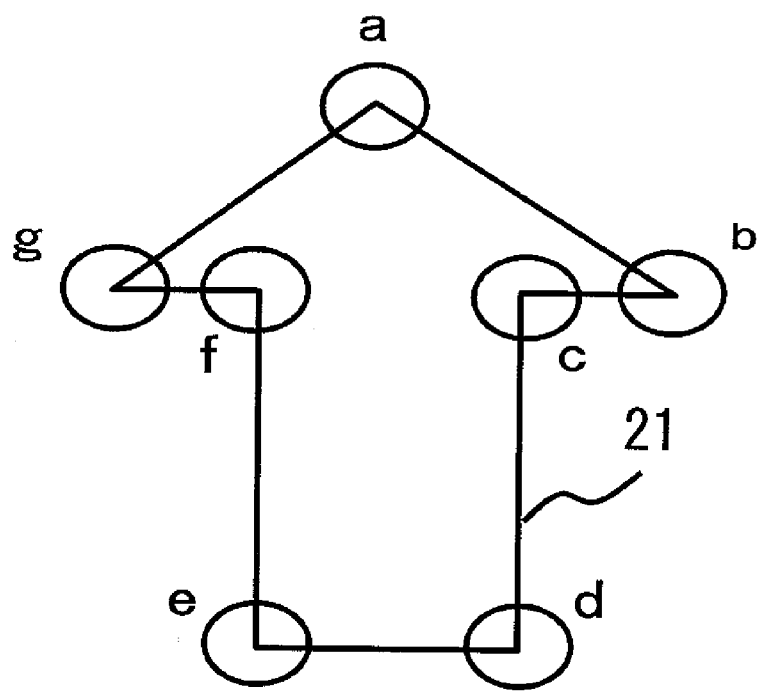
FIG. 2 shows a reference pattern and a reticle pattern according to a first embodiment of the present invention.

Embodiments of the present invention will be described below in detail with reference to the accompanying drawings.

FIG. 1 is a block diagram of a pattern-defect inspection apparatus according the present invention.

As shown in FIG. 1, the pattern-defect inspection apparatus includes a reticle 1, an X-Y stage 2, a reticle-illumination light source 3, an objective lens 4, a half mirror 5, a CCD (charge-coupled device) image sensor 6, an image acquiring unit 7, a comparing unit 8, an image processor 9, a stage controller 10, a reference-data generator 11, an inspection-sensitivity setting unit 12, a defect determining unit 13, and a defect storage unit 14.

As shown in FIG. 1, the reticle 1 to be inspected is fixed to the X-Y stage 2. For defect inspection, a surface of the reticle 1 is divided into multiple inspection areas and inspection is performed for each inspection area. In accordance with an instruction from the stage controller 10, the X-Y stage 2 moves to scan the surface of the reticle 1 in X and Y directions for each inspection area.

The CCD image sensor 6 and an illumination optical system, which includes the reticle-illumination light source 3, the half mirror 5, and the objective lens 4, are disposed above the X-Y stage 2. Light emitted from the reticle-illumination light source 3 is reflected by the half mirror 5, is concentrated by the objective lens 4, and is then incident on the reticle 1. The reflected light passes through the objective lens 4 and the half mirror 5 and is captured by the CCD image sensor 6. The captured light is then sent to the image acquiring unit 7 as image signals. The image acquiring unit 7 converts the image signals, sent from the CCD image sensor 6, into a reticle pattern that serves as an inspection pattern. The converted reticle pattern is input to the comparing unit 8.

On the other hand, of design data of the reticle pattern, design data corresponding to each inspection area of the reticle 1 is received by the reference-data generator 11 in synchronization with a scan area of the X-Y stage 2. The stage controller 10 controls the X-Y stage 2 and also sends information of the scan area of the X-Y stage 2 to the reference-data generator 11.

Reference data received by the reference-data generator 11 is sent to the image processor 9 and is converted into a reference pattern. This reference pattern corresponds to the above-described reticle pattern (actual pattern) generated by the image acquiring unit 7. The reference pattern generated by the image processor 9 in such a manner is input to the comparing unit 8.

The comparing unit 8 compares the reticle pattern with the shape of the reference pattern. When a mismatched portion exists, the comparing unit 8 detects its position coordinates and its pattern mismatch width. The detected mismatch information is sent to the defect determining unit 13. The "mismatch information" herein refers to information containing the coordinates of a portion where the mismatch (i.e., a pattern difference) occurs and the amount of mismatch (i.e., the amount of difference).

The defect determining unit 13 determines whether or not the pattern-mismatch width sent from the comparing unit 8 exceeds a predetermined threshold. When the pattern-mismatch width exceeds the threshold, the defect determining unit 13 determines that the mismatched portion is defective and causes the defect storage unit 14 to store the position coordinates of the detective portion. In this case, the predetermined threshold is set as a reference for determining whether or not a portion in question is defective. The threshold is used to determine inspection sensitivity for pattern defect inspection and is set for each inspection area by the inspection-sensitivity setting unit 12. Thereafter, the set value (the threshold value set for each inspection area) is reported to the defect determining unit 13.

In the present invention, the inspection sensitivity is adjusted according to the complexity of the pattern.

First Embodiment

An example in which the inspection sensitivity is adjusted will now be described with reference to FIGS. 2 and 3. In this example, the number of corner portions in a pattern (hereinafter referred to as a "corner-portion count") is used as an indicator representing the complexity of the pattern shape, and the threshold is varied based on whether or not the corner-portion count exceeds a predetermined value.

In this embodiment, the inspection-sensitivity setting unit 12 sets the threshold to 20 nm for a pattern whose corner-portion count of the reference pattern exceeds five and sets the threshold to 5 nm for a pattern whose corner-portion count of the reference pattern does not exceed five. The set value is then reported to the defect determining unit 13.

Figure 2B:
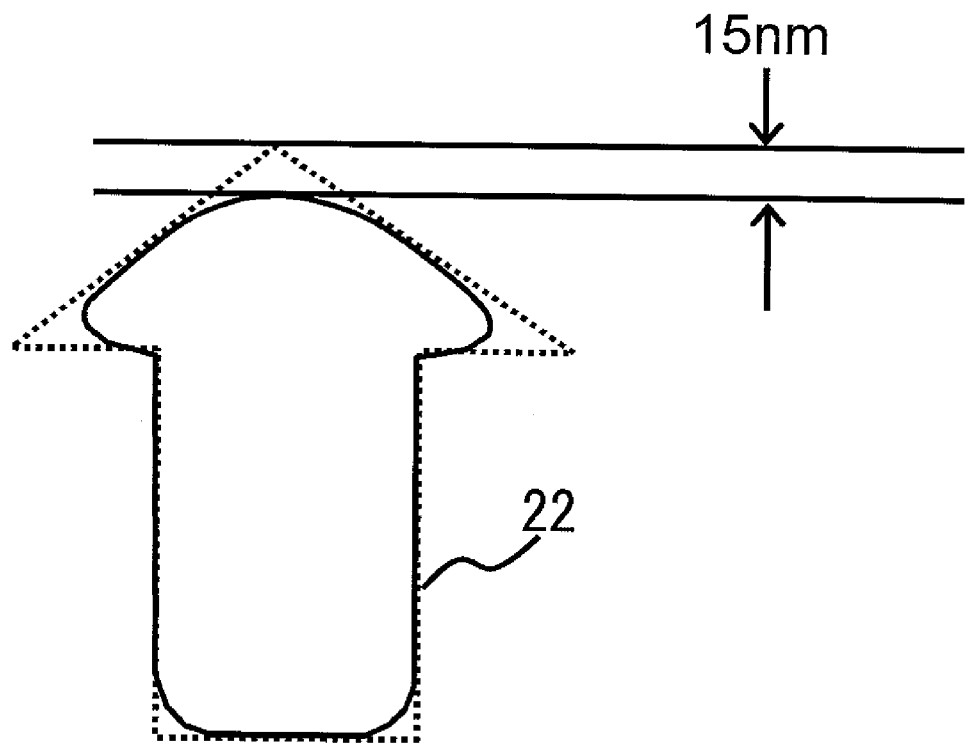

FIG. 2A shows a reference pattern 21 included in one inspection area, and FIG. 2B shows a reticle pattern 22, which is an actual pattern corresponding to the reference pattern 21. The reference pattern 21 has a total of seven corner portions at positions a to g surrounded by circles. For ease of illustration of portions that do not match the reference pattern 21 and the mismatch widths thereof, the reference pattern 21, which is shown by a dotted line, is drawn superimposed on the reticle pattern 22 in coordinates in which the reticle pattern 22 shown FIG. 2B is drawn.

The comparing unit 8 compares the reference pattern 21 and the reticle pattern 22 to detect a pattern-mismatch width for each corner portion. For example, as shown in FIG. 2B, a pattern-mismatch width detected at the corner portion a is 15 nm.

In the case, since the corner-portion count of the reference pattern 21 is seven, the threshold is set to 20 nm. Thus, since the pattern-mismatch width at the corner portion a does not exceed the threshold "20 nm", the defect determining unit 13 determines that the corner portion a is not defective and does not notify the defect storage unit 14 about the corner portion a. Similar determinations are also performed on the other corner portions b to g.

Figure 3A:
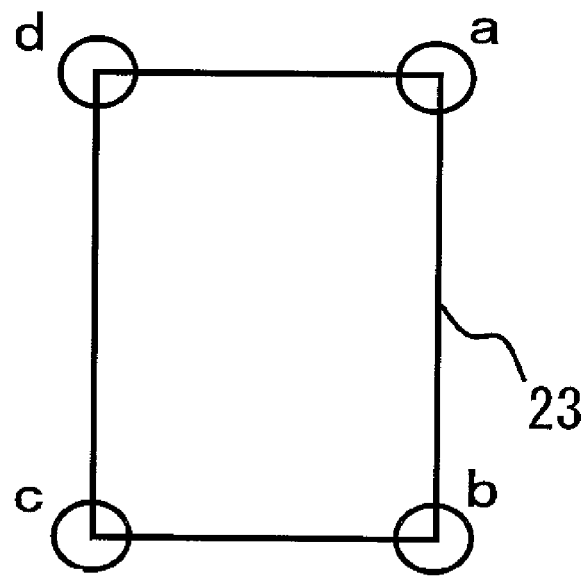
FIG. 3 shows a reference pattern and a reticle pattern according to the first embodiment of the present invention.
Figure 3B:
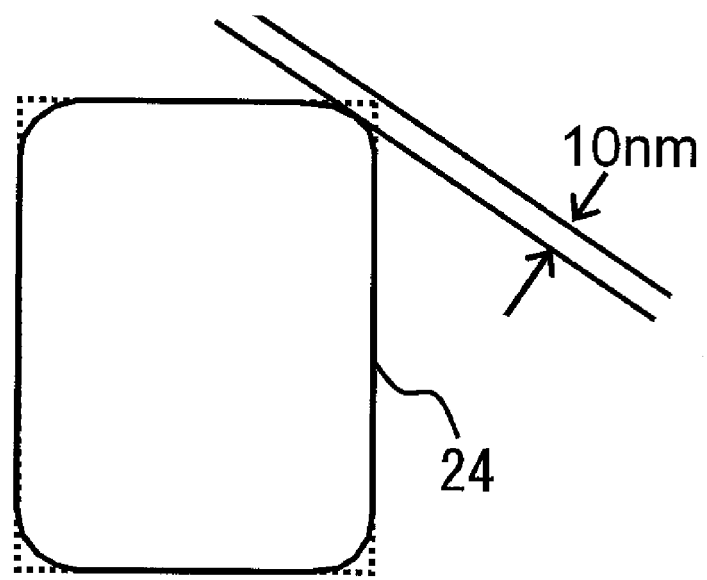

FIG. 3A shows a reference pattern 23, which is different from the reference pattern 21 shown in FIG. 2, and FIG. 3B shows a reticle pattern 24 corresponding to the reference pattern 23. As in FIG. 2B, for ease of illustration of a pattern difference from the reference pattern 23, the reference pattern 23, which is shown by a dotted line, is drawn superimposed on the reticle pattern 24 in coordinates in which the reticle pattern 24 is drawn. It can be seen from FIG. 3 that the pattern-mismatch width detected at the corner portion a is 10 nm.

In this example, since the corner-portion count of the reference pattern 23 is four, the threshold is set to 5 nm. Thus, the mismatch width between the reference pattern 23 and the reticle pattern 24 exceeds the threshold "5 nm", the defect determining unit 13 determines that the corner portion a is defective (although the maximum mismatch width is 10 nm) and notifies the defect storage unit 14 about the position coordinates of the corner portion a. Similar processing is also performed on other corner portions b, c, and d.

As described above, according to the present embodiment, it is determined that the reticle pattern 22 having a mismatch width of 20 nm is not defective, whereas it is determined that the reticle pattern 24 having a mismatch width of 10 nm is detective. These are results obtained considering a difference in the shapes of the reticle patterns 22 and 24, thereby making it possible to make an appropriate defect-determination compared to the known inspection method.

A reason why the above-described determination is more advantageous than the known inspection method will be described below. For example, in the case of the reticle pattern 22 shown in FIG. 2, since the corner-portion count in the reference pattern exceeds a predetermined value, it is highly likely that reticles that are determined as pattern mismatches (pattern differences) contain false defects that are not supposed to be processed as defects. Accordingly, in this case, the threshold is reduced so that the inspection sensitivity decreases, so as to prevent reticles that are highly likely to be false defects from being extracted from reticles that can be detected as pattern mismatches (pattern differences). Consequently, it is possible to selectively detect reticles that are highly likely to be defective.

Although not particularly described in the present embodiment, detection-sensitivity adjustment as described above is typically performed on a predetermined specified area (or a specified pattern).

In the present embodiment, since it is satisfactory if the number of false defects decreases, it is permissible if areas that are determined to be defective contain false defects with respect to areas for which a threshold for high inspection sensitivity has been set, as in the example shown in FIG. 3B.

It is also desired that, with respect to an area for which a threshold for the lowest detection sensitivity is set, the threshold be set such that portions that are determined to be non-defective contain absolutely no defect (i.e., such that a failure in extracting a defect does not occur).

Second Embodiment

Next, in the pattern defect inspection using the pattern-defect inspection apparatus shown in FIG. 1, an angle of a pattern corner portion instead of the corner-portion count is used as an indicator representing the complexity of the pattern shape. A description in this embodiment will be given of an example in which the threshold is varied based on whether or not the angle exceeds a predetermined value.

In this example, when the angle of a corner portion in a reference pattern does not exceed 90°, the inspection-sensitivity setting unit 12 sets the threshold to 20 nm. When the angle exceeds 90°, the inspection-sensitivity setting unit 12 sets the threshold to 5 nm, which is smaller than the threshold "20 nm". The inspection-sensitivity setting unit 12 notifies the defect determining unit 13 about the set values.

Figure 4A:
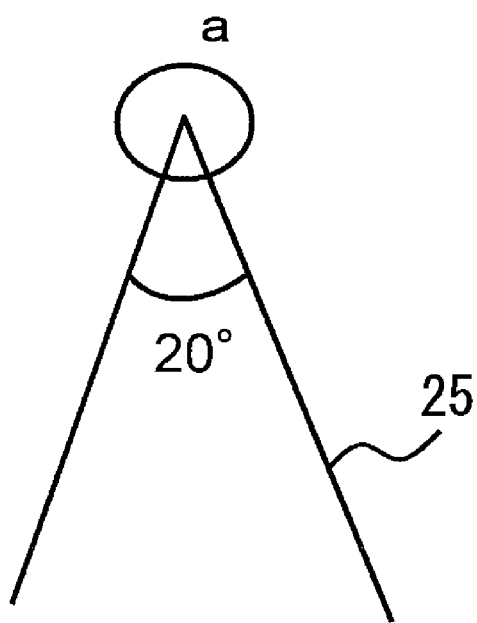
FIG. 4 shows a reference pattern and a reticle pattern according to a second embodiment of the present invention.
Figure 4B:
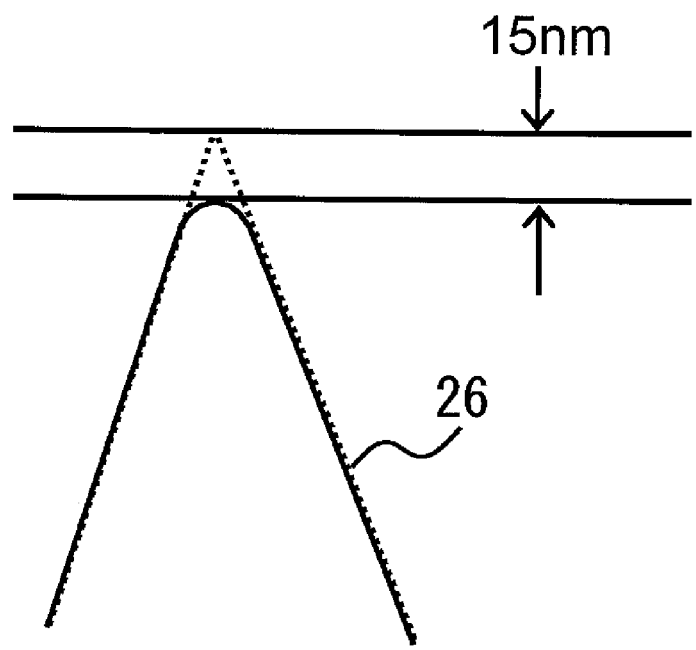

FIG. 4A shows a reference pattern 25 included in one inspection area, and FIG. 4B shows a reticle pattern 26 corresponding to the reference pattern. In FIG. 4B, for ease of understanding a difference between the reference pattern 25 and the reticle pattern 26, as in FIG. 2B, the reference pattern 25 is drawn superimposed on the reticle pattern 26 by a dotted line. Since the angle of a corner portion a in the illustrated reference pattern 25 is 20° and thus does not exceed 90°, the threshold is set to 20 nm.

The comparing unit B compares the reference pattern 25 and the reticle pattern 26 to detect a mismatch width therebetween. In this case, as shown in part (b) in FIG. 4, the pattern-mismatch width at the corner portion a is 15 nm. Since the pattern-mismatch width at the corner portion a does not exceed the threshold "20 nm", the defect determining unit 13 determines the corner portion a is not defective and does not notify the defect storage unit 14 about the corner portion a.

Figure 5A:
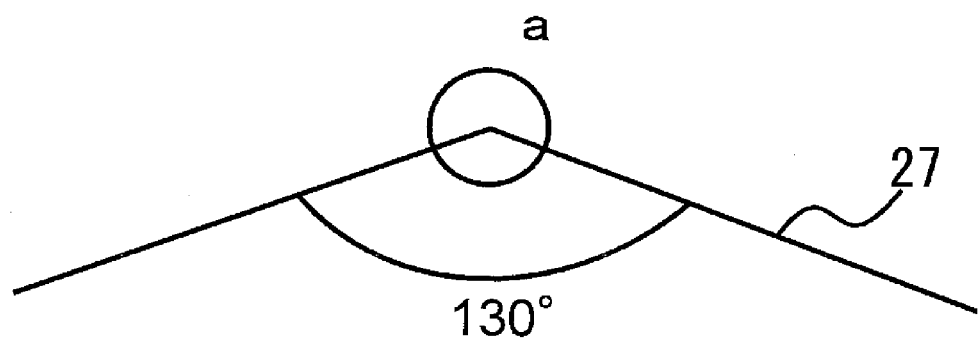
FIG. 5 shows a reference pattern and a reticle pattern according to the second embodiment of the present invention.
Figure 5B:
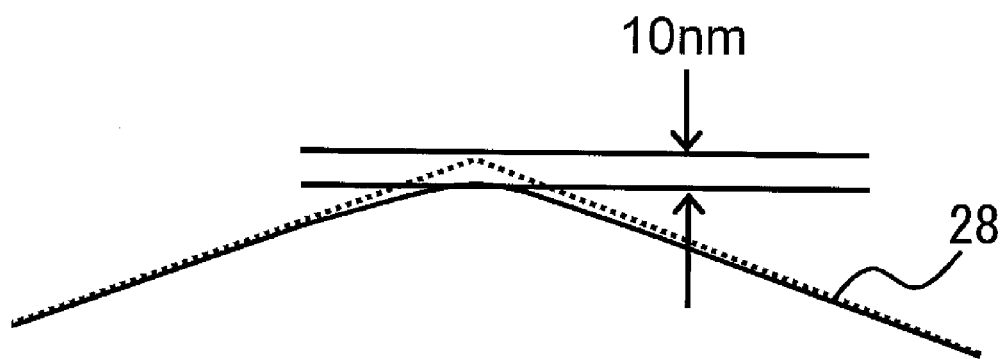

FIG. 5A shows a reference pattern 27, which is different from the reference pattern 25 shown in FIG. 4, and FIG. 5B shows a reticle pattern 28 corresponding to the reference pattern 27. In coordinates in which the reticle pattern 28 is drawn, the reference pattern 27, which is shown by a dotted line, is drawn superimposed on the reticle pattern 28. It can be seen from FIG. 5B that the pattern-mismatch width detected at the corner portion a is 10 nm.

In this example, since the angle at a corner portion a in the reference pattern 27 is 130°, the threshold is set to 5 nm. Thus, the mismatch width in the reticle pattern 28 exceeds 5 nm, the defect determining unit 13 determines that the corner portion a is defective and notifies the defect storage unit 14 about the position coordinates of the corner portion a.

As shown in FIGS. 4 and 5, the mismatch width in the pattern generally increases as the angle of a corner portion in the pattern decreases. The reason for the occurrence of such a phenomenon is that, as the angle of a corner portion in a pattern decreases, the pattern shape is more susceptible to the influence of photolithography and etching. In this case, detected mismatch widths do not necessary indicate that all thereof act as defects, and thus, setting the inspection sensitivity as described above in the present embodiment makes it possible to reduce the number of false detects.

Third Embodiment

Examples in which the inspection sensitivity is adjusted will now be described with reference to FIGS. 6 and 7. In this embodiment, the distance between adjacent corner portions in a reference pattern is used as an indicator representing the complexity of the pattern shape, and the threshold is varied based on whether or not the distance exceeds a predetermined value.

In the pattern defect inspection of this embodiment, the pattern-defect inspection apparatus shown in FIG. 1 is also used. In this example, when the distance between adjacent corner portions in a reference pattern does not exceed 50 nm, the inspection-sensitivity setting unit 12 sets the threshold to 20 nm. When the distance exceeds 50 nm, the inspection-sensitivity setting unit 12 sets the threshold to 5 nm, which is smaller than the threshold "20 nm". The inspection-sensitivity setting unit 12 then notifies the defect determining unit 13 about the set values.

Figure 6A:
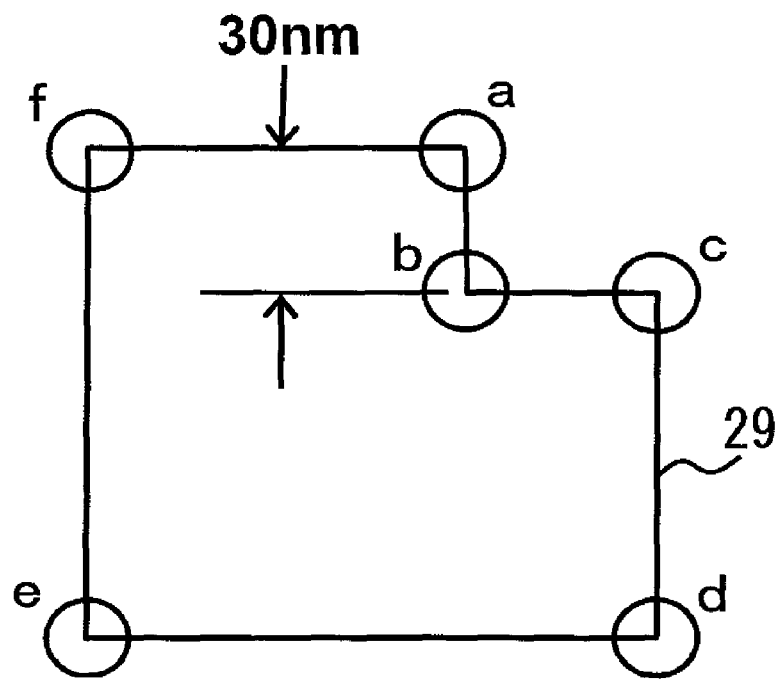
FIG. 6 shows a reference pattern and a reticle pattern according to a third embodiment of the present invention.
Figure 6B:
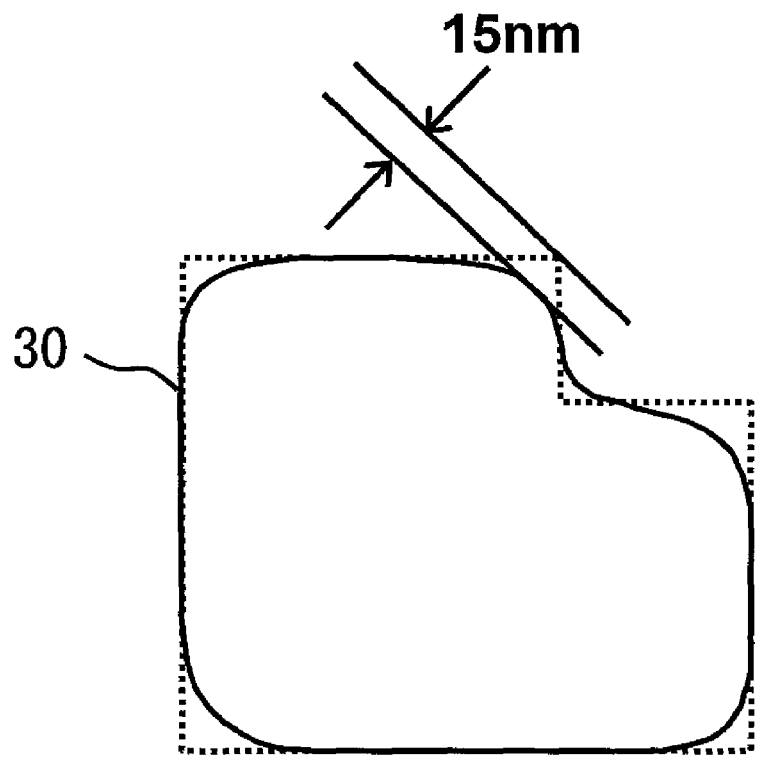

FIG. 6A shows a reference pattern 29 included in one inspection area, and FIG. 6B shows a reticle pattern 30 corresponding to the reference pattern 29. In coordinates in which the reticle pattern 30 is drawn, the reference pattern 29, which is shown by a dotted line, is drawn superimposed on the reticle pattern 30. When the distance between adjacent corner portions a and b in the reference pattern 29 is assumed to be 30 nm, the threshold is set to 20 nm since the distance does not exceed 50 nm.

The comparing unit 8 compares the reference pattern 29 and the reticle pattern 30 to detect a mismatch width therebetween. As shown in FIG. 6B, the pattern-mismatch width at the corner portion a is 15 nm. Since the pattern-mismatch width at the corner portion a does not exceed the threshold "20 nm", the defect determining unit 13 determines the corner portion a is not defective and thus does not notify the defect storage unit 14 about the corner portion a.

In this case, the defect determining unit 13 may notify the defect storage unit 14 about information indicating that no defect exists.

Figure 7A:
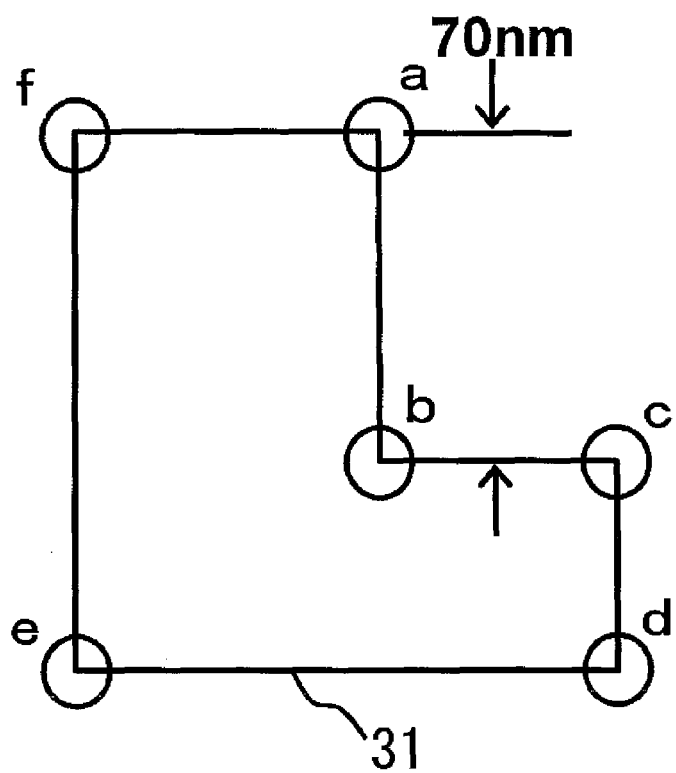
FIG. 7 shows a reference pattern and a reticle pattern according to the third embodiment of the present invention.
Figure 7B:
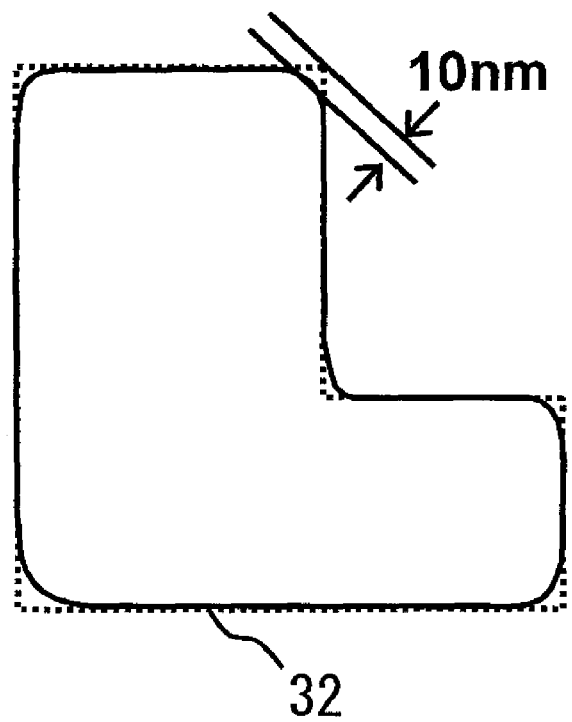

FIG. 7A shows a reference pattern 31, which is different from the reference pattern 29 shown in FIG. 6A, and FIG. 7B shows a reticle pattern 32 corresponding to the reference pattern 31. In coordinates in which the reticle pattern 32 in FIG. 7B is drawn, the reference pattern 31, which is shown by a dotted line, is drawn superimposed on the reticle pattern 32. It can be seen from FIG. 7B that the pattern-mismatch width detected at the corner portion a is 10 nm. In this example, when the distance between adjacent corner portions a and b in the reference pattern 31 is assumed to be 70 nm, the threshold is set to 5 nm since the distance exceeds 50 nm. Thus, since the mismatch width in the reticle pattern 32 exceeds the threshold "5 nm", the defect determining unit 13 determines that the corner portion a is defective and notifies the defect storage unit 14 about the position coordinates of the corner portion a.

In general, when the distance between adjacent corner portions decreases, a mutual interference between the patterns increases and the pattern mismatch width thus increases. However, with respect to corner portions detected in such a situation, the likelihood that they are defective becomes relatively small even when the mismatch width is large (since they are false defects in most cases). Thus, setting the inspection sensitivity as described above in the present embodiment makes it possible to reduce the number of false detects.

Fourth Embodiment

Examples in which the inspection sensitivity is adjusted will now be described with reference to FIGS. 8 and 9. In this embodiment, a width of a reference pattern, i.e., a dimension in a direction orthogonal to the longitudinal direction of the pattern is used as an indicator representing the complexity of the pattern shape, and the threshold is varied based on whether or not the dimension exceeds a predetermined value.

In the pattern defect inspection of this embodiment, the pattern-defect inspection apparatus shown in FIG. 1 is also used.

Figure 8A:
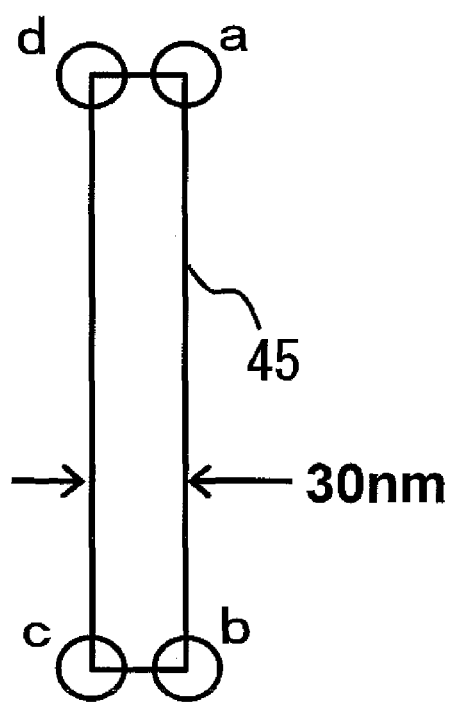
FIG. 8 shows a reference pattern and a reticle pattern according to a fourth embodiment of the present invention.
Figure 8B:
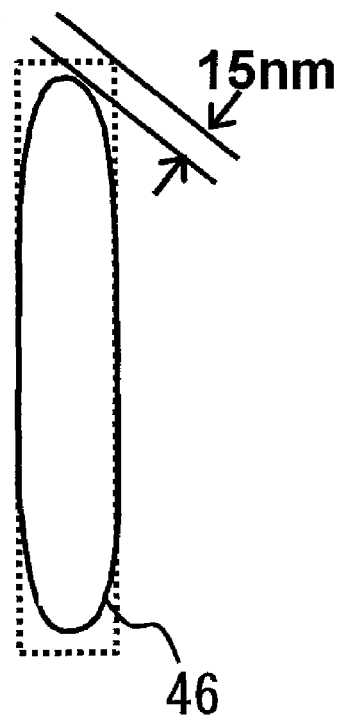
Figure 9A:
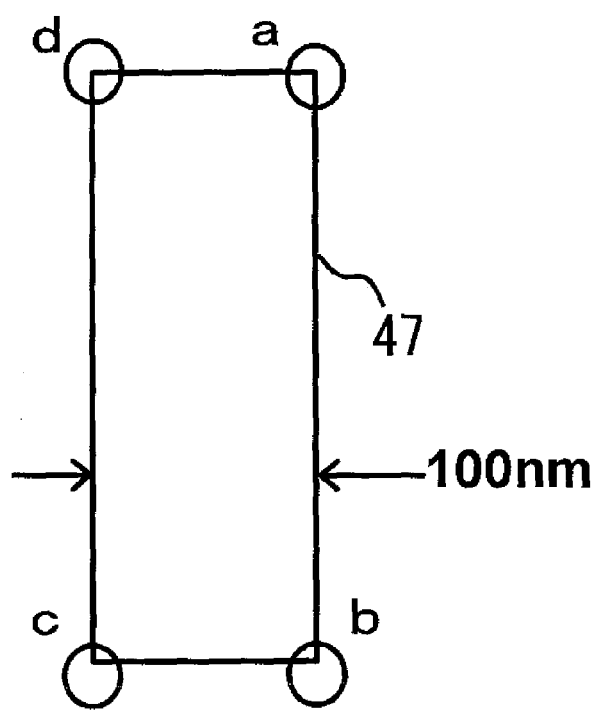
FIG. 9 shows a reference pattern and a reticle pattern according to the fourth embodiment of the present invention.

In this example, FIG. 8A shows a reference pattern 45 included in one inspection area, and FIG. 8B shows a reticle pattern 46 corresponding to the reference pattern 45. In FIG. 8B, in coordinates in which the reticle pattern 46 is drawn, the reference pattern 45, which is shown by a dotted line, is drawn superimposed on the reticle pattern 46. In this case, as shown, the width of the reference pattern 45 is assumed to be 30 nm.

Figure 9B:
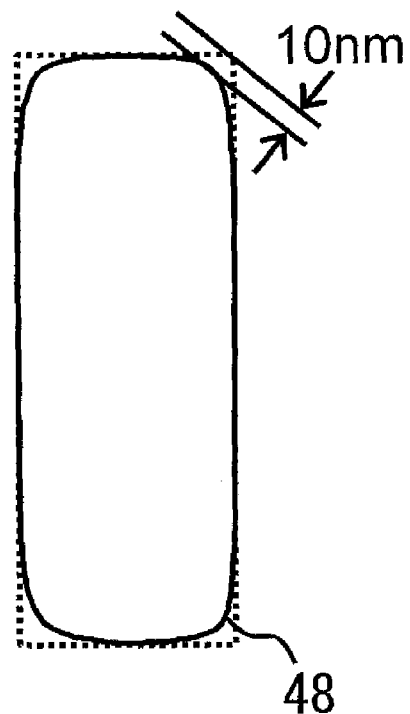

Similarly, FIG. 9B shows a reference pattern 47 included in one inspection area, and FIG. 9B shows a reticle pattern 48 corresponding to the reference pattern 47. In FIG. 9B, in coordinates in which the reticle pattern 48 is drawn, the reference pattern 47, which is shown by a dotted line, is drawn superimposed on the reticle pattern 48. In this case, as shown, the width of the reference pattern 47 is assumed to be 100 nm.

In this embodiment, the inspection-sensitivity setting unit 12 sets the threshold to 20 nm when the width of the reference pattern does not exceed 50 nm, and sets the threshold to 5 nm when the width of the reference pattern exceeds 50 nm. The inspection-sensitivity setting unit 12 notifies the defect determining unit 13 about the set values.

As shown in FIG. 8B, although the pattern-mismatch width at a corner portion a is 15 nm, the defect determining unit 13 determines that the corner portion a is not defective since the pattern mismatch width does not exceed the threshold "20 nm". Thus, the inspection-sensitivity setting unit 12 does not notify the defect storage unit 14 about information regarding the corner portion a.

On the other hand, as shown in FIG. 9B, although the pattern-mismatch width at a corner portion a is 10 nm, the defect determining unit 13 determines that the corner portion a is defective since the pattern mismatch width at the corner portion a exceeds the threshold "5 nm". Thus, the inspection-sensitivity setting unit 12 notifies the defect storage unit 14 about mismatch information regarding the corner portion a.

As in the third embodiment, when the pattern width decreases, a mutual interference between the patterns increases and the pattern mismatch width thus increases. Thus, as described above, corner portions detected as pattern mismatches are false defects in most cases (even if the mismatch pattern is larger), and the likelihood that they are defective becomes relatively small. Thus, setting the inspection sensitivity low (i.e., setting loose sensitivity) makes it possible to reduce the number of false detects.

Fifth Embodiment

A flow for the inspection according to the present invention will now be described with reference to FIGS. 10 to 17. The block diagram (shown in FIG. 1) for the pattern-defect inspection apparatus is also used to describe the pattern defect inspection in this embodiment.

FIG. 10 is an inspection flow according to the present invention. The inspection flow includes three main flows up to image-data combination (step S131) illustrated at the center in FIG. 10, and the three flows will be described first.

Flow (1)

The flow at the left side in FIG. 10 shows a procedure for obtaining inspection data. In the flow, image data 105 of inspection data is obtained through processing of data conversion (1) and data conversion (2).

Figure 11A:
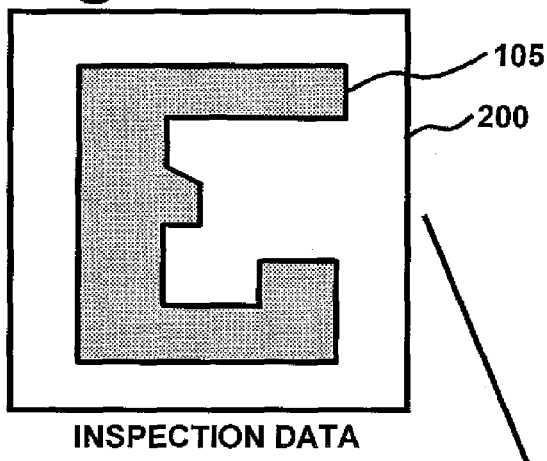
FIG. 11 shows an example of combination of image data according to the fifth embodiment of the present invention.

More specifically, first, the reference-data generator 11 extracts only data required for inspection from design data 101, and converts the format of the extracted data into a format for apparatus inspection (in step S102) to create design data for inspection (the design data will herein be referred to as "inspection design data 103"). The reference-data generator 11 then sends the inspection design data 103 to the image processor 9. Subsequently, the image processor 9 converts the format of the inspection design data 103 into the format of the image data 105 (in step S104). The inspection data 105 having the converted image data is sent to the comparing unit 8. FIG. 11A shows one example of the inspection data 105.

Flow (2)

The flow at the right side in FIG. 10 shows a procedure for obtaining image data of an actual pattern (a reticle pattern) formed on a reticle.

Specifically, a reticle 1 is first placed on the X-Y stage 2 of the inspection apparatus (in step S121). Subsequently, inspection conditions for the inspection-sensitivity setting unit 12 and so on are set (in step S122). Pattern defect inspection is then started (in step S123).

Next, in accordance with an instruction from the stage controller 10, the stage 2 is moved (in step S124) so that a reticle-pattern scan operation (reticle scan) can be performed. The shape of the reticle pattern is then captured by the image acquiring unit 7 (in step S125). Image signals indicating the captured reticle-pattern shape are converted by the image acquiring unit 7 into a reticle pattern 126, which serves as image data to be inspected. The reticle pattern 126 is then sent to the comparing unit 8. FIG. 11C shows one example of the reticle pattern 126.

Next, the comparing unit 8 compares the image data 105 of the inspection data and the image data 126 of the reticle pattern.

The comparing unit 8 determines whether or not the reticle 1 is properly placed on the stage 2. When the reticle 1 is properly placed, the comparing unit 8 closely compares the image data 105 of the inspection data and the image data 126 of the reticle pattern.

Specifically, for example, an alignment pattern (not shown) provided on the reticle 1 is used to check whether or not the image data 105 and the image data 126 generally match each other (in step S130).

When they do not match each other, the process returns to step S124, in which the scan operation for capturing a reticle pattern is performed again. In this case, the processing may be redone from the operation (step S121) for placing the reticle 1 on the stage 2.

When the image data 105 and the image data 126 match each other, a result of the comparison is sent to the defect determining unit 13. Examples of the result sent to the defect determining unit 13 include information (mismatch information), such as coordinates of a portion where the pattern mismatch occurs and the mismatch width.

The detect determining unit 13 then combines the image data 105 of the inspection data and the image data 126 of the reticle pattern and closely compares both data (in step S131).

Flow (3)

The flow at the center in FIG. 10 shows a procedure for obtaining inspection-sensitivity data.

Specifically, the inspection-sensitivity setting unit 12 first receives the inspection design data 103 sent from the reference-data generator 11. The inspection-sensitivity setting unit 12 then extracts a specific area 210 based on the received inspection data 103 (in step S112).

The processing for extracting the information of the specific area 210 is performed by, for example, the following method.

First, before the specific area 210 is extracted, a specific area according to the pattern shape is determined. That is, which area is to be specified as the specific area is associated with a feature of the pattern shape.

Next, the information of the associated specific area 210 is pre-stored in a storage unit (not shown).

Lastly, during the extraction of the specific area 210, the feature of the pattern shape obtained from the inspection design data 103 is sent to the storage unit. Thereafter, the information of the specific area 210 according to the feature of the pattern shape is obtained from the storage unit.

The processing for extracting the specific area 210 may be performed by an operator, instead of the use of the storage unit provided in the system, as described above. That is, the arrangement may be such that operator checks the pattern shape of the inspection design data 103, creates information of the specific area desired by him/her, and inputs the information of the specific information 210 (created by him/her) to the inspection apparatus.

Subsequently, inspection-sensitivity data 114 is created based on the obtained information of the specific area 210 (in step S113). Specifically, a threshold for determining inspection sensitivities for the specific area and other areas is set. Inspection-sensitivity data 114 for which inspection sensitivities that are different from each other depending on areas are set is completed.

Processing for setting the inspection sensitivity data 114 is performed by, for example, the following method.

For example, before the inspection sensitivity data 114 is created, what kind of threshold is to be set is predetermined for each condition (such as the number of corner portions in the reference pattern, the angle of each corner portion, or the distance between adjacent corner portions). In this case, for each condition, different thresholds are set for the specific area and areas other than the specific area.

Next, information regarding the thresholds is stored in the storage unit (not shown).

Lastly, during the creation of the inspection-sensitivity data 114, the pattern-shape feature obtained from the inspection design data 103 is sent to the storage unit. Subsequently, information regarding the threshold corresponding to the feature of the pattern shape is obtained from the storage unit.

The processing for creating the inspection-sensitivity data 114 may be performed by the operator, instead of the use of the storage unit provided in the system, as described above. That is, the arrangement may be such that the operator checks the pattern shape of the inspection design data 103, creates information sensitivity data 114 desired by him/her, and inputs the information of the inspection sensitivity data 114 (created by him/her) to the inspection apparatus.

The inspection sensitivity data 114 created by the inspection-sensitivity setting unit 12 as described above is sent to the defect determining unit 13.

Next, the defect determining unit 13 combines the three types of image data created in flows (1) to (3) and performs fault determination (in step S131).

Figure 11B:
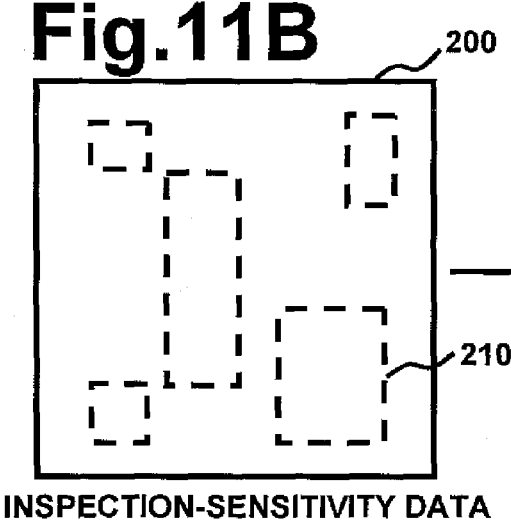
Figure 11C:
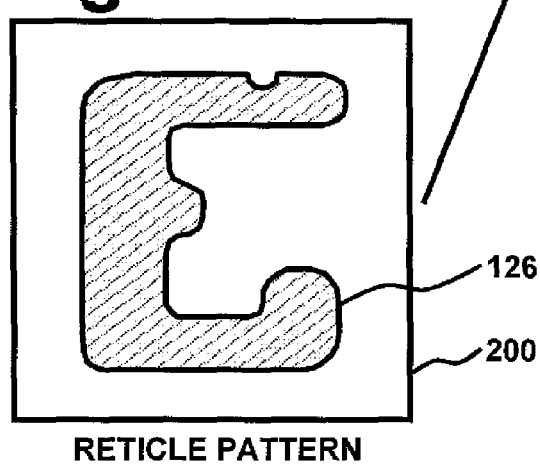
Figure 11D:
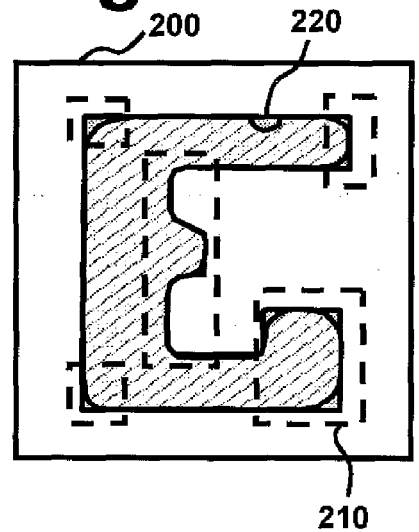

Specifically, the inspection data 105 shown in FIG. 11A, the reticle pattern 126 shown in FIG. 11B, and the inspection sensitivity data 114 in FIG. 11C are superimposed on an image, as shown in FIG. 11D.

In the case of FIG. 11D, only one defect 220 is detected as a defect. In this case, any pattern difference in each specific area 210 indicated by a thick dotted line is not detected as a defect. Frames 200 in FIG. 11A to FIG. 11D represent minimum areas for inspection and have the same area.

Figure 12:
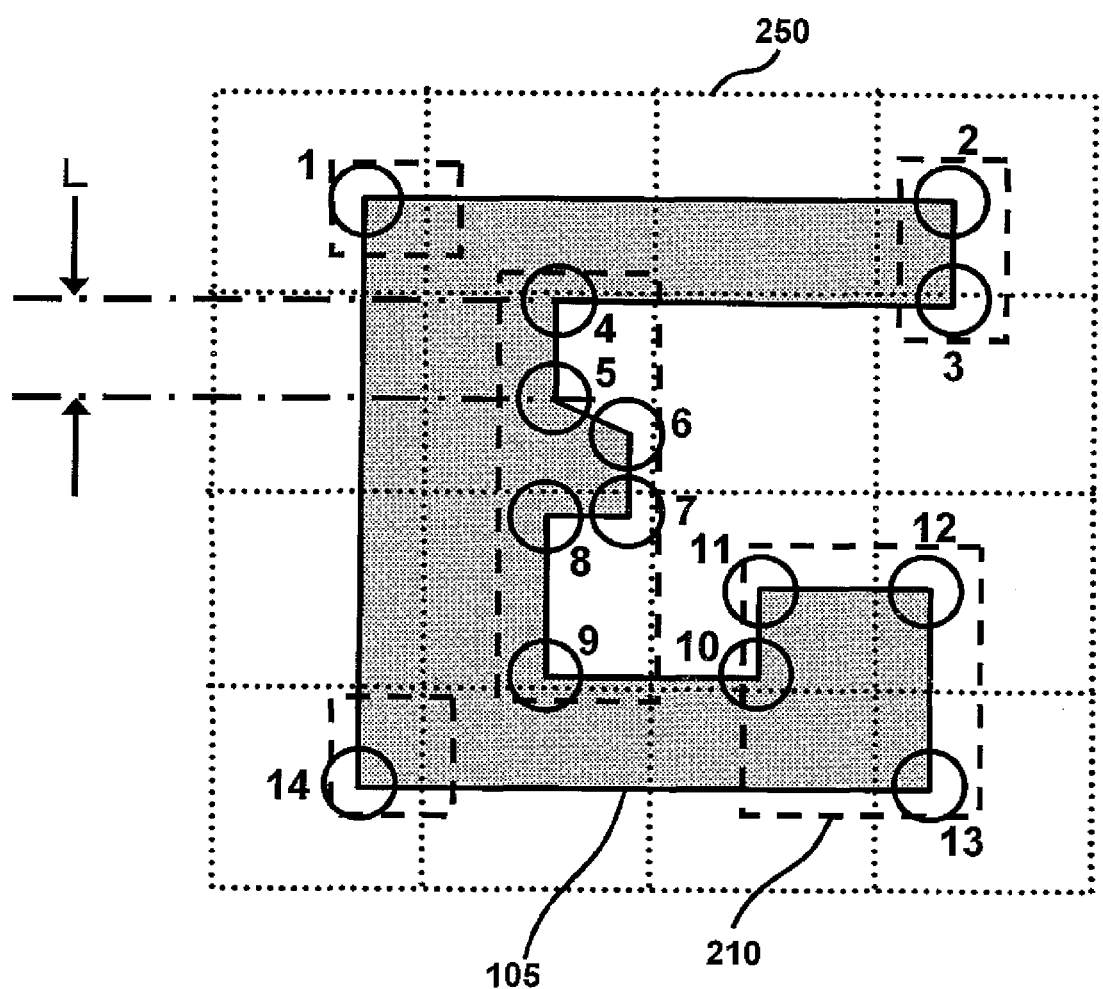
FIG. 12 shows a specific example for setting inspection sensitivity in a grid pattern according to the fifth embodiment of the present invention.

FIG. 12 shows a specific example for setting the inspection sensitivity in a grid pattern.

In FIG. 12, areas denoted by circles (i.e., corner portions 1 to 14) represent all corner portions in the inspection data 105. Each area defined by a square indicated by a thick dotted line represents the specific area 210.

On the other hand, a grid 250 indicated by a thin dotted line represents a micro inspection area to be subjected to the inspection. In this manner, the inspection sensitivity is typically set for each divided area.

Figure 13E:
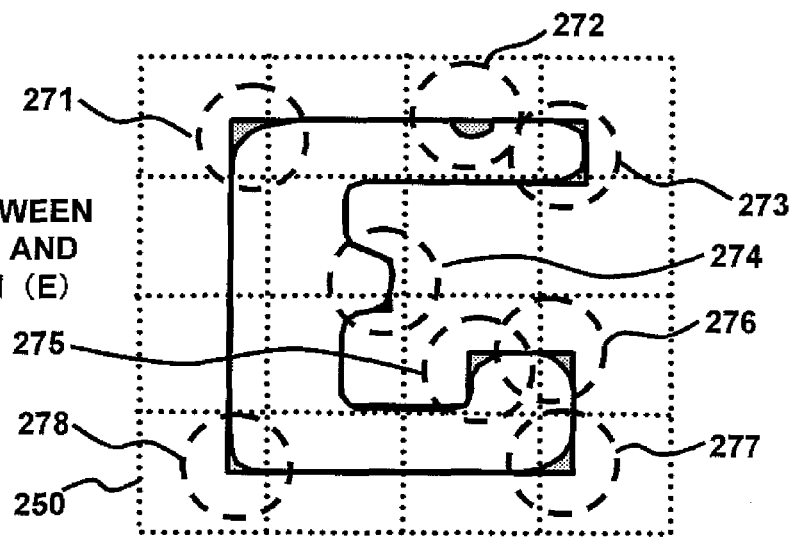
FIG. 13 shows a specific example of a method for detecting a defect according to the fifth embodiment of the present invention.
Figure 13F:
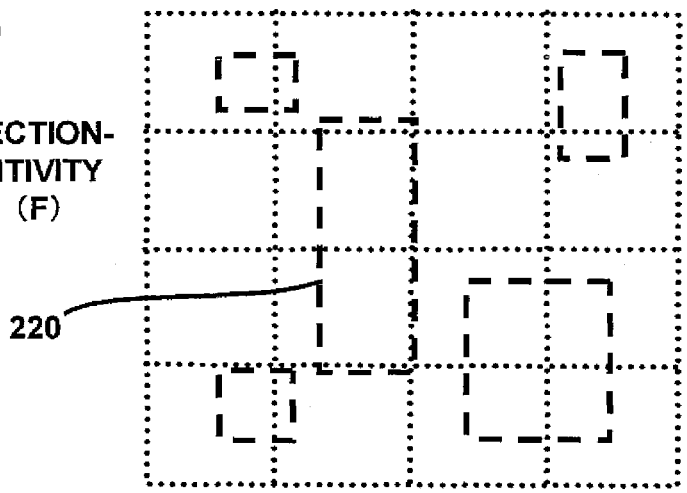
Figure 13G:
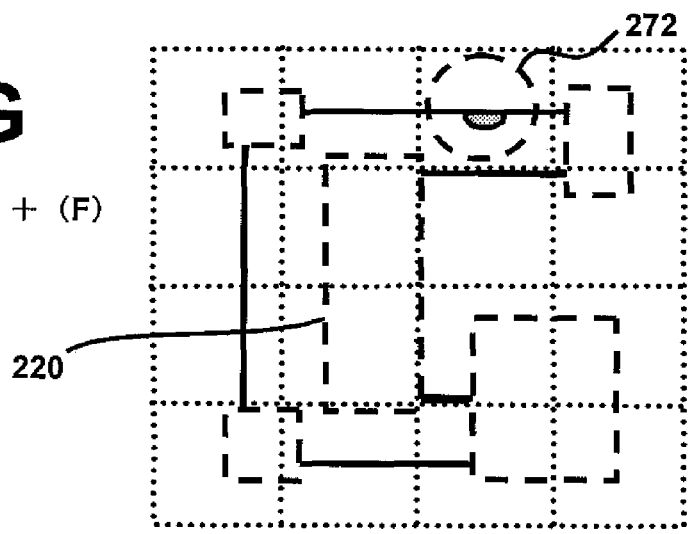

FIG. 13 shows a specific example of a method for detecting a defect.

FIG. 13E shows data in which the inspection data and a reticle pattern are superimposed. Eight portions 271 to 278 denoted by circles indicated by thick dotted lines are portions where pattern differences between the inspection data 105 and the reticle pattern 126 exist.

FIG. 13F shows data of the inspection sensitivity. In part (f), each area surrounded by a thick dotted line represents a specific area 220. The threshold is set so that the inspection sensitivity for the specific area 220 is lower than the area outside the specific area 220.

FIG. 13D shows data in which the data shown in part (e) and FIG. 13F are superimposed. As a result of superimposition in this manner, only one portion 272 is detected as a defect.

Figure 14A:
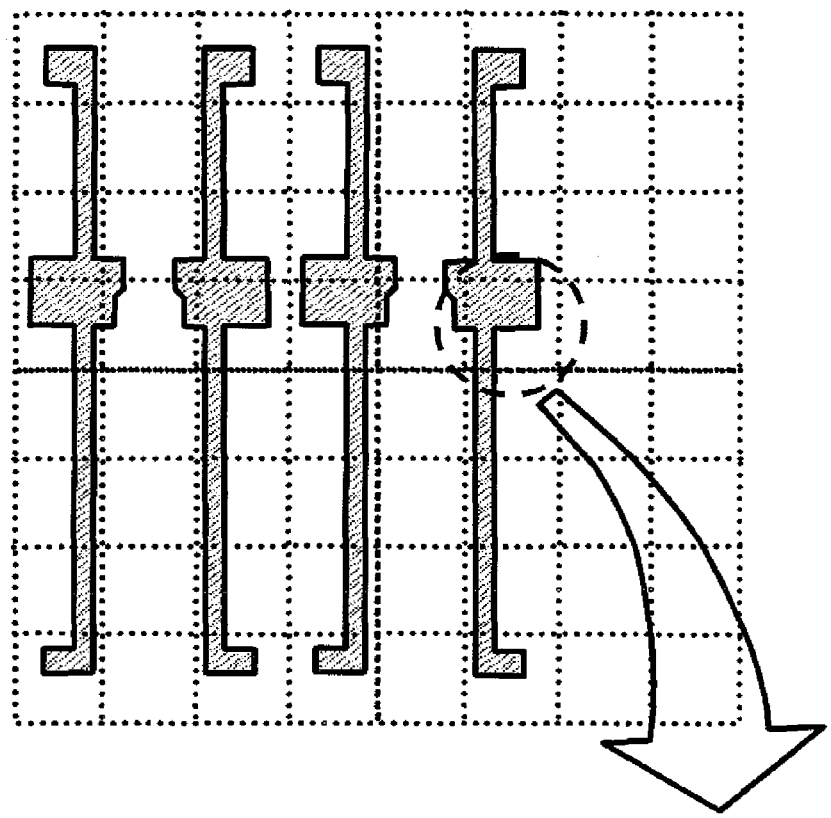
FIG. 14 shows an example in which an inspection target is set for each micro inspection area according to the fifth embodiment of the present invention.

FIG. 14 shows an example in which an inspection target is set for each micro inspection area.

As shown in FIG. 14, when a micro inspection area is divided, corner portions that should not be recognized as targets of an inspection condition are produced.

Figure 14B:
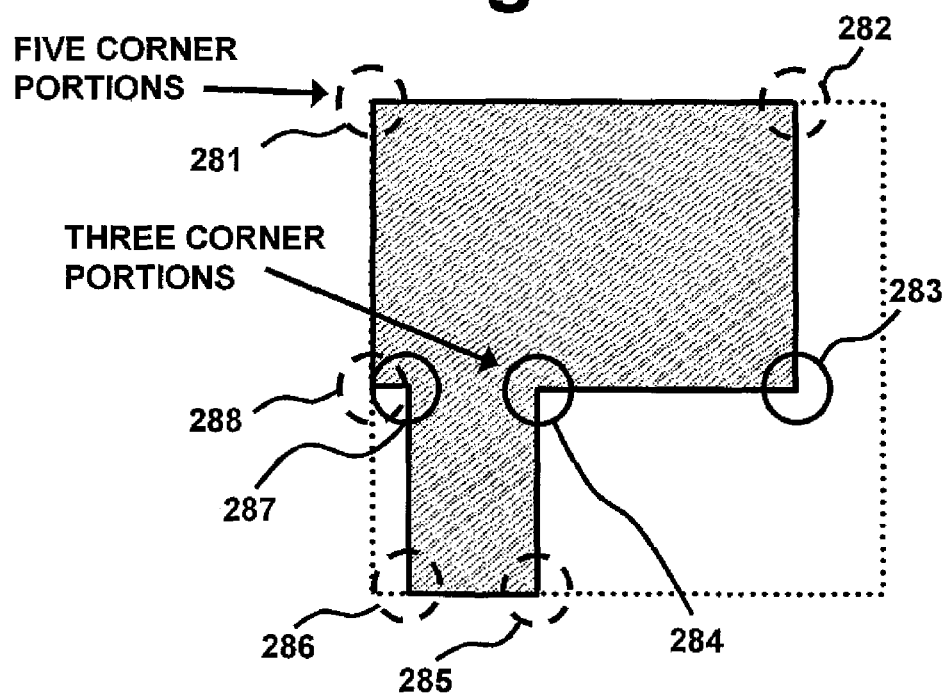

Specifically, in the enlarged diagram in FIG. 14B, eight corner portions 281 to 288 exist. However, five corner portions 281, 282, 285, 286, and 288 of the eight portions have been recognized as corners as a result of the division of the inspection area was into micro inspection areas. That is, in practice, the five corner portions are not corner portions of the pattern, and thus should not be recognized as targets for an inspection condition.

Accordingly, for example, data between adjacent micro inspection areas are compared with each other in order to determine whether or not each corner portion is an authentic corner portion. Specifically, when the result of the comparison indicates that corner portions that exist at the same coordinates in both micro inspection areas, the corner portions are excluded from targets of an inspection condition. Then, only corner portions other than the corner portions excluded from the targets are recognized as targets of an inspection condition, so that only authentic corner portions can be extracted.

In this example, three corner portions 283, 284, and 287 surrounded by solid-line circles are recognized as targets of an inspection condition.

FIG. 15 shows an example in which a false defect and a defect bare distinguished from each other based on the number of corner portions. For ease of understanding this embodiment, FIG. 15 shows an example in which a shape A and a shape B in a reticle pattern are formed to have substantially the same pattern shape. The use of this embodiment allows the shape B and the shape A in the reticle pattern to be recognized as a defect and a false defect, respectively.

Figure 16:
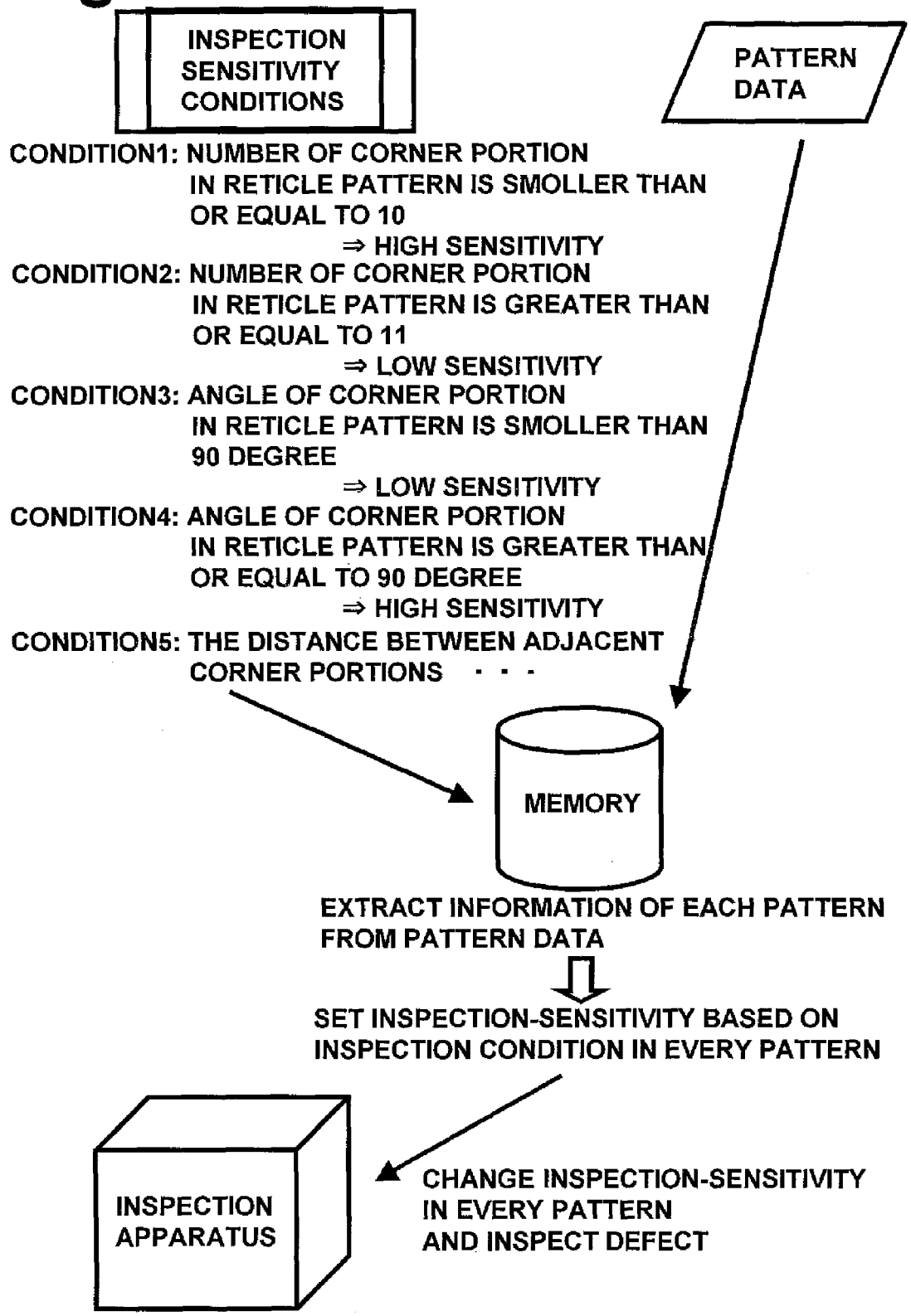
FIG. 16 shows a specific example of inspection sensitivity conditions according to the fifth embodiment of the present invention.

FIG. 16 shows a specific example of inspection sensitivity conditions. As shown, for example, multiple conditions 1 to 5 (or more) are set as inspection sensitivity conditions. In this manner, inspection conditions can also be set in combination to perform fault inspection.

With the method described above, the defect determining unit 13 (in the inspection flow shown in FIG. 10) makes a determination (in step S132) as to whether or not a pattern defect exists, based on the comparison result sent from the comparing unit 8 and the inspection sensitivity data sent from the inspection-sensitivity setting unit 12.

When a pattern defect is found, information regarding the pattern defect is sent to the defect storage unit 14, in which the information is then stored (in step S133). The information regarding the pattern defect includes, for example, coordinates on the reticle or semiconductor wafer.

When any pattern defect is not found, a determination is made (in step S134) as to whether or not the reticle inspection is to be continued. For example, when an area that requires the inspection still remains, the process returns to the scan operation (step S124) for capturing a reticle pattern and the inspection is continued.

When any area that requires the inspection does not remain, the reticle defect inspection is completed (in step S135).

After the reticle defect inspection is finished as described above, it is checked whether or not a portion recognized as a pattern defect is really a pattern defect. Thereafter, a portion that is really a pattern defect is then repaired.

For example, the checking process and the repairing processing described above can be performed through the use of a focused ion beam (FIB) apparatus. The FIB apparatus focuses an ion beam, obtained from a gallium ion source, to 5 to 10 nm and irradiates a subject with the focused beam. In the pattern repairing process, for example, a reticle pattern defective portion is repaired by emitting the defective portion with the ion beam while blowing a gas serving as material.

The above described are descriptions for the first to fifth embodiments.

Figure 17:
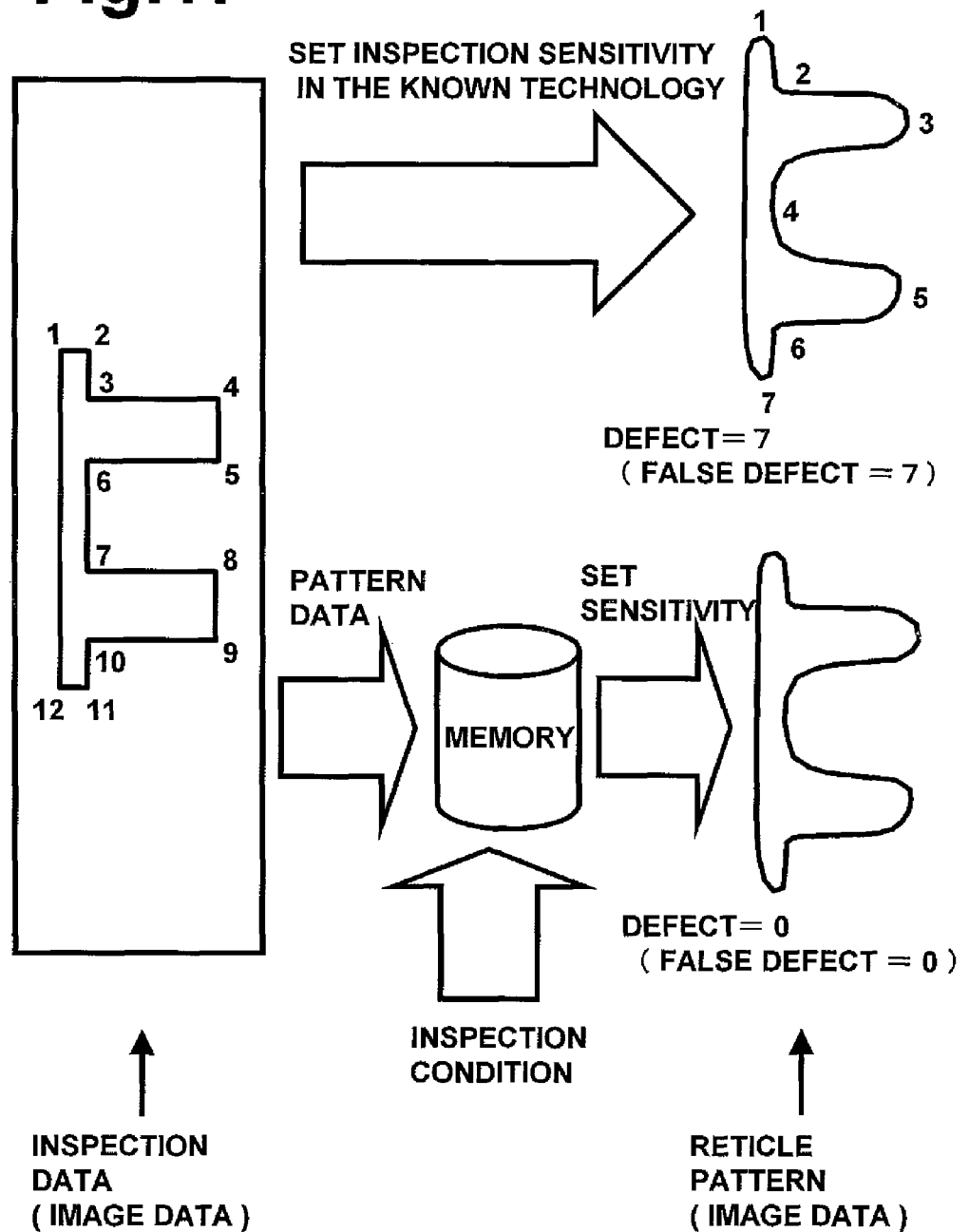
FIG. 17 shows advantages of the setting of inspection sensitivity based on the inspection conditions.

Advantages when the first to fifth embodiments are implemented will now be described with reference to FIG. 17. FIG. 17 shows advantages obtained by setting inspection sensitivity based on the inspection condition.

As shown in FIG. 17, the total number of corner portions in inspection data 114 is 12. In this case, with respect to a reticle pattern 126 corresponding to the inspection data 114, all corner portions have pattern differences but the number of defects is zero.

In the case of FIG. 17, when the inspection sensitivity is set as in the known technology, some of the 12 corner portions are recognized as defects, as shown. For example, in this case, seven portions 1 to 7 are recognized as defects. That is, in this case, one corner portion in each of the portions 1 to 7 is recognized as a defect. All of the seven corner portions recognized as detects are false defects.

In contrast, when the inspection conditions according to the present invention are used to adjust the setting of the inspection sensitivity, the sensitivity for the seven portions 1 to 7 is set low, so that the number of portions recognized as defects becomes zero. In this case, therefore, the number of detected defects becomes equal to the number of actual defects.

In the above embodiments, the descriptions have been given of:
1) an example in which the number of corner portions of a pattern is used as an indicator representing the complexity of the pattern shape and the threshold is set based on whether or not the number of corner portions of the pattern exceeds a predetermined value;
2) an example in which the threshold is varied based on whether or not the angle of an corner portion in a pattern exceeds a predetermined value;
3) an example in which the threshold is varied based on whether or not the distance between adjacent corner portions in a reference pattern exceeds a predetermined value, and
4) an example in which the threshold is varied based on whether or not a pattern width in a reference pattern exceeds a predetermined value. However, the use of the indicators in combination also makes it possible to set more practical detection sensitivity.

Although the descriptions in the above embodiments have been given of reticle patterns by way of example, similar defect inspection can also be performed on a pattern formed on a semiconductor wafer.

According to above set forth embodiment, during the defect inspection of a complex micro pattern formed on a substrate the inspection sensitivity is varied in accordance with the complexity (for example number of corner portion and so on) of the pattern. Thus, compared to the known technology, the inspection sensitivity can be more appropriately set. Additionally, the pattern-defect inspection method of the present invention makes it possible to achieve a significant reduction in the number of false defects and is also advantageous in improving the inspection sensitivity and reducing the inspection time.

The present invention is applicable to inspecting defects in patterns formed on semiconductor wafers or inspecting defects in patterns of reticles for use in the pattern formation of semiconductor ICs.

What is claimed is:

1. A pattern-defect inspection method for a plurality of pattern on a substrate, the method comprising:
    extracting information of an image of a pattern on the substrate to be inspected;
    providing information of an image of a reference pattern from design information, the reference pattern corresponding to the pattern to be inspected;
    determining an inspection sensitivity in accordance with the number of corner portions of the reference pattern;
    comparing the information of the image of the pattern to be inspected and the information of the image of the reference pattern; and
    detecting a defect of the pattern, using a computer on a basis of both the inspection sensitivity and a comparison result obtained by the comparing the information of the image of the pattern to be inspected and the information of the image of the reference pattern.

2. The pattern-defect inspection method according to claim 1, wherein the inspection sensitivity is set lower for patterns in which the number of corner portions is greater than a predetermined value than for patterns in which the number of corner portions is smaller than or equal to the predetermined value.

3. The pattern-defect inspection method according to claim 2, wherein the predetermined value is set according to a shape of the reference pattern to be compared.

4. The pattern-defect inspection method according to claim 1, further comprising:
    extracting association information associated with the number of the corner portions and the inspection sensitivity before the detecting;
    wherein, the inspection sensitivity is adjusted on the basis of the association information.

5. The pattern-defect inspection method according to claim 1, wherein a result of the comparing is mismatch information including coordinates of each portion where a pattern difference exists and an amount of the difference.

6. The pattern-defect inspection method according to claim 1, wherein the corner portion is counted except one or more corner portions on a border line of adjacent two predetermined areas for inspection.

7. A pattern-defect inspection method for a plurality of pattern on a substrate, the method comprising:
    extracting information of an image of a pattern on the substrate to be inspected;
    providing information of an image a reference pattern from design information, the reference pattern corresponding to the pattern to be inspected;
    determining an inspection sensitivity in accordance with an angle of a corner potion of the reference pattern;
    comparing the information of the image of the pattern to be inspected and the information of the image of the reference pattern; and
    detecting a defect of the pattern, using a computer, on the basis of both the inspection sensitivity and a comparison result obtained by the comparing the information of the image of the pattern to be inspected and the information of the image of the reference pattern.

8. The pattern-defect inspection method according to claim 7, wherein the inspection sensitivity is set lower for patterns in which the angle of the corner portion is smaller than or equal to the predetermined value than for patterns in which the angle of the corner portion is greater than the predetermined value.

9. A pattern-defect inspection method for a plurality of pattern on a substrate, the method comprising:
    extracting information of an image of a pattern on the substrate to be inspected;
    providing information of an image of the a reference pattern from design information, the reference pattern corresponding to the pattern to be inspected;
    determining an inspection sensitivity in accordance with a distance between adjacent corner potions of the reference pattern;
    comparing the information of the image of the pattern to be inspected and the information of the image of the reference pattern; and
    detecting a defect of the pattern, using a computer, on a basis of both the inspection sensitivity and the comparison result obtained by the comparing the information of the image of the pattern to be inspected and the information of the image of the reference pattern.

10. The pattern-defect inspection method according to claim 9, wherein the inspection sensitivity is set lower for patterns in which the distance between adjacent corner potions is smaller than or equal to the predetermined value than for patterns in which the distance between adjacent corner potions is greater than a predetermined value.

* * * * *